United States Patent [19]

Shelley et al.

[11] 4,229,477

[45] Oct. 21, 1980

[54] PHARMACEUTICAL COMPOSITIONS CONTAINING BROMHEXINE AND METHOD OF TREATING DIABETIC NEPHROPATHY THEREWITH

[75] Inventors: Julian H. Shelley, Newbury; John R. Clamp; Martin Hartog, both of Bristol, all of England

[73] Assignee: Boehringer Ingelheim GmbH, Ingelheim am Rhein, Fed. Rep. of Germany

[21] Appl. No.: 42,286

[22] Filed: May 25, 1979

[30] Foreign Application Priority Data

May 26, 1978 [GB] United Kingdom ............... 23189/78

[51] Int. Cl.³ .......................................... A61K 31/135
[52] U.S. Cl. .................................................. 424/330
[58] Field of Search ...................................... 424/330

[56] References Cited

FOREIGN PATENT DOCUMENTS

| | | |
|---|---|---|
| 968254 | 9/1964 | United Kingdom ..................... 424/330 |
| 1178034 | 1/1970 | United Kingdom ..................... 424/330 |
| 1464082 | 2/1977 | United Kingdom ..................... 424/330 |

*Primary Examiner*—Frederick E. Waddell
*Attorney, Agent, or Firm*—Hammond & Littell, Weissenberger & Muserlian

[57] ABSTRACT

Pharmaceutical compositions for the treatment of diabetic nephropathy containing bromhexine and a method of treating diabetic nephropathy therewith.

3 Claims, No Drawings

PHARMACEUTICAL COMPOSITIONS CONTAINING BROMHEXINE AND METHOD OF TREATING DIABETIC NEPHROPATHY THEREWITH

This invention relates to pharmaceutical compositions for use in the treatment of diabetic nephropathy.

BACKGROUND OF THE INVENTION

Diabetic nephropathy is a frequent complication of diabetes mellitus. It is generally believed that thickening of the glomerular basement membranes is responsible for kidney damage.

Glycoproteins perform a decisive role in the structure of basement membranes, the carbohydrate portion of such glycoproteins being linked to the apoprotein principally through asparagine and hydroxylysine residues. It is known that in diabetics the amount of hydroxyproline, hydroxylysine and saccharide part of the glycoproteins in the basement membranes of the kidney is increased as compared with normal healthy subjects (see Diabetes 25, 909–913 [1976]).

DESCRIPTION OF THE INVENTION

The present invention is based on our discovery that the metabolism of glycoproteins by diabetics may be substantially normalized, that is, the proportion of saccharide and glycopeptide excreted strongly reduced to levels equivalent to those of a normal healthy subject, by the administration of N-(2-amino-3,5-dibromo-benzyl)-N-methyl-cyclohexylamine or non-toxic, pharmaceutically acceptable acid addition salt thereof. For this purpose, N-(2-amino-3,5-dibromo-benzyl)-N-methyl-cyclohexylamine or a pharmaceutically acceptable acid addition salt thereof is administered in dosages of from 15 to 30 mg each, 3 to 4 times per day.

This effect is in contradistinction to the effect of these compounds on healthy subjects, where the amount of saccharide and glycopeptide excreted (molecular fraction: M 500–10,000) increases.

N-(2-amino-3,5-dibromo-benzyl)-N-methyl-cyclohexylamine and its acid addition salts, as well as processes for their preparation, are described in British Pat. No. 968,254, where they are stated to possess a secretolytic activity, in addition to antitussive, monoamine oxidase inhibiting and antipyretic activities, when administered in dosages of from 0.5 to 10 mg. preferably 2.0 to 4.0 mg. The antiulcer activity of these compounds when administered in higher dosages of from 30 to 100 mg, preferably 35 to 60 mg, has also previously been described in British Pat. No. 1,464,082.

According to one aspect of the present invention, there are provided novel pharmaceutical dosage unit compositions comprising, as the active ingredient, N-(2-amino-3,5-dibromo-benzyl)-N-methyl-cyclohexylamine or a non-toxic, pharmaceutically acceptable acid addition salt thereof in association with a pharmaceutical carrier or excipient, each dosage unit containing from 15 to 30 mg of active ingredient. Particularly preferred compositions according to the invention are those wherein each dosage unit contains about 24 mg of active ingredient.

The active ingredient, preferably N-(2-amino-3,5-dibromo-benzyl)-N-methyl-cyclohexylammonium chloride (known under the generic name bromhexine) may be incorporated in the usual pharmaceutical preparations especially those for oral administration such as, for example, tablets, coated tablets, capsules and syrups. The carriers and excipients may be those customarily employed in pharmaceutical compositions such as, for example, talcum, gum arabic, lactose, starch, magnesium stearate, aqueous or non-aqueous vehicles, fatty substances of animal or vegetable origin, paraffin derivatives, glycols, various wetting, dispersing or emulsifying agents and/or preservatives.

The compositions according to the invention may conveniently be presented in a container together with written or printed directions to use the compositions in the treatment of diabetic nephropathy. The said container may, for example, be a bottle, an ampule or a vial. If desired, the container may itself bear printed or written directions for the intended use of the product. Alternatively, or additionally, the container may be accompanied by separate written or printed directions for use such as, for instance, a leaflet describing the intended medical use of the product concerned. Such leaflets are frequently referred to as "package inserts" and may, for example, recommend daily doses, mention possible side effects and provide other information useful to a medical practitioner.

According to a further aspect of the present invention, there is provided a novel method of treating patients suffering from diabetic nephropathy, which comprises administering to the patient an effective amount of N-(2-amino-3,5-dibromo-benzyl)-N-methyl-cyclohexylamine or a non-toxic pharmaceutically acceptable acid addition salt thereof.

The effect of N-(2-amino-3,5-dibromo-benzyl)-N-methyl-cyclohexylammonium chloride (Bromhexine) on glycoprotein metabolism was determined as follows:

24 hour collections were made from 8 normal healthy humans (4 women and 4 men) and 8 diabetics (1 woman and 7 men) before and after a 3 to 4 week period of treating each subject orally 3 times with 24 mg of bromhexine. A 20% by volume aliquot was taken from each urine specimen and freeze-dried.

The dried material (ca 1 gm) was dissolved in the minimum quantity of distilled water and the solution was chromatographed with water on a Sephadez G-50 column (length: 148 cm; diameter: 3.4 cm). The carbohydrate-containing fraction was collected and subjected to ultrafiltration using a UM-05 membrane (Amicon Ultrafiltration Cell-Model 202). The filtrate obtained was again freeze-dried.

The dried material (ca 1 mg) was analyzed for carbohydrate, using gas-liquid chromatography. In this procedure, the sample, together with internal standards, was first subjected to methanolysis with 1.0 M HCl in dry methanol (0.5 ml) for 24 hours at 85° C. The resulting solution was neutralized and then treated with acetic acid anhydride (0.05 ml) for 6 hours. On completion of the treatment the solution obtained was centrifuged, and the supernatant liquid was transferred to a clean flask, dried and stored in a dessicator. When required for gas chromatography, the dried material was triturated with a trimethylsilylating mixture, and the resulting trimethylsilyl ethers of the methyl glycosides were subjected to gas chromatography (140°–200° C. at 0.5° C./min.).

The 8 diabetics had a mean age of 42.5 years (24–66 years) and an average duration of diabetes of 11.75 years (4–19 years). 5 patients were maintained on insulin, 2 on oral hypoglycemic agents and 1 on diet alone. Diabetic treatment was not changed during the study. 3 patients suffered varying degrees of retinopathy, 1 had ischaemic heart disease and 1 had intermittent proteinuria.

The 8 normal subjects had a mean age 25.28 years (23–47 years).

The following table shows the results obtained:

|  | HEALTHY SUBJECTS | | DIABETICS | |
| --- | --- | --- | --- | --- |
|  | before treatment | after treatment | before treatment | after treatment |
| 24 - Hour Volume (ml) | 1,281 | 1,406 | 1,694 | 1,686 |
| Total dry weight (gm) | 36.3 | 44.0 | 102.6 | 110.7 |
| Fraction dry weight (gm) | 4.2 | 4.4 | 8.7 | 6.1 |
| Carbohydrate content ($\mu$Mol/24 hours) | | | | |
| Fucose | 121 | 224 | 259 | 203 |
| Glucuronic acid | 1,085 | 1,573 | 1,854 | 987 |
| Mannose | 121 | 169 | 205 | 121 |
| Galactose | 258 | 364 | 616 | 383 |
| Glucose | 329 | 425 | 12,609 | 7,241 |
| N-Acetylglucosamine | 204 | 287 | 313 | 181 |
| N-Acetylgalactosamine | 139 | 196 | 264 | 176 |
| N-Acetylneuraminic acid | 94 | 147 | 195 | 145 |

As may be seen from the table, before treatment, the diabetic subjects excreted significantly more carbohydrate-containing material than the normal subjects. After treatment, the normal subjects showed an insignificant rise in the urinary excretion of carbohydrate-containing material, whereas the diabetic subjects showed a considerable decrease in the excretion of such material.

As described in British Pat. No. 968,254, the acute oral toxicity of bromhexine has been shown to be >3 gm/Kg in mice (0 out of 10 animals died).

The following non-limiting examples serve to illustrate the present invention.

EXAMPLE 1

Tablets containing 24 mg of N-(2-amino-3,5-dibromo-benzyl)-N-methyl-cyclohexylammonium chloride Composition:
1 Tablet contains:

| Active ingredient | 24.0 mg |
| --- | --- |
| Lactose | 148.0 mg |
| Corn starch | 60.0 mg |
| Gelatin | 6.0 mg |
| Magnesium stearate | 2.0 mg |
|  | 240.0 mg |

Method of preparation

The active ingredient was admixed with the lactose and corn starch, and the mixture was homogeneously moistened with an aqueous 10% solution of the gelatin. The mixture obtained was granulated through a screen of 1.5 mm mesh size, dried and again passed through the same screen. The granulate thus obtained was admixed with the magnesium stearate and pressed into 240 mg-tablets.

EXAMPLE 2

Coated tablets containing 24 mg of N-(2-amino-3,5-dibromo-benzyl)-N-methyl-cyclohexylammonium chloride Method of preparation:

The tablet cores were prepared analogous to Example 1. The cores were then covered with a coating consisting essentially of a mixture of sugar and talcum.

EXAMPLE 3

Capsules containing 24 mg of N-(2-amino-3,5-dibromo-benzyl)-N-methyl-cyclohexylammonium chloride 1 capsule contains:

| Active ingredient | 24.0 mg |
| --- | --- |
| Lactose | 61.0 mg |
| Corn starch | 34.0 mg |
| Magnesium stearate | 1.0 mg |
|  | 120.0 mg |

Method of preparation

The ingredients were intimately admixed, and 120 mg-portions of the mixture were filled into hard gelatin capsules of appropriate size.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of treating diabetic nephropathy in a human patient, which comprises administering to said patient an effective amount of N-(2-amino-3,5-dibromo-benzyl)-N-methyl-cyclohexylamine or a non-toxic, pharmaceutically acceptable acid addition salt thereof.

2. The method of claim 1, where said effective amount is 15 to 30 mg 3 to 4 times daily.

3. The method of claim 1, where said effective amount is 24 mg 3 to 4 times daily.

* * * * *